United States Patent
Biel (12)

(10) Patent No.: US 6,623,513 B2
(45) Date of Patent: Sep. 23, 2003

(54) APPARATUS AND METHOD OF PHOTODYNAMIC ERADICATION OF ORGANISMS UTILIZING PYRROLNITRIN

(75) Inventor: Merrill A. Biel, Mendota Heights, MN (US)

(73) Assignee: Advanced Photodynamic Technologies, Inc., Minneapolis, MN (US)

( * ) Notice: Subject to any disclaimer, the term of this patent is extended or adjusted under 35 U.S.C. 154(b) by 0 days.

(21) Appl. No.: 10/052,990

(22) Filed: Jan. 18, 2002

(65) Prior Publication Data

US 2002/0165594 A1 Nov. 7, 2002

Related U.S. Application Data

(60) Provisional application No. 60/263,125, filed on Jan. 19, 2001.

(51) Int. Cl.[7] .................................................. A61N 5/06

(52) U.S. Cl. ........................... 607/88; 607/89; 128/898

(58) Field of Search ....................... 607/88–89

(56) References Cited

U.S. PATENT DOCUMENTS

| 6,149,671 A | * | 11/2000 | Nordquist et al. | ............ 607/89 |
| 6,251,127 B1 | * | 6/2001 | Biel | ............................ 607/88 |
| 6,290,712 B1 | * | 9/2001 | Nordquist et al. | ............ 607/88 |
| 6,344,050 B1 | * | 2/2002 | Chen | ............................ 607/88 |

* cited by examiner

Primary Examiner—Roy D. Gibson
Assistant Examiner—Henry M. Johnson, III
(74) Attorney, Agent, or Firm—Fulbright & Jaworski, L.L.P.

(57) ABSTRACT

The invention relates to a method of photoeradication of cellular and acellular organisms including the steps of providing a photosensitive material and pyrrolnitrin in association with a cellular or acellular organism and applying light in association with the cellular or acellular organism to cause a disruption of the organism. The method according to the present invention may be utilized in invitro and invivo treatment protocols for infections, sterilization procedures, cancer cell eradication, virus and fungus eradication, spore eradication, and biofilm organism eradication. Additional aspects of the invention include particular combinations of photosensitive materials, pyrrolnitrin, and optional surfactants for use in photodynamic therapies.

55 Claims, 4 Drawing Sheets

Eradication of *Aspergillus flavus*[a] on a filter material using methylene blue and pyrrolnitrin mediated photodynamic therapy.

| Nr. | Methylene Blue (μg/mL) | Pyrrolnitrin (μg/mL) | Power[b] (mW) | Dose Rate (mW/cm$^2$) | Light Dose (J/cm$^2$) | Time (sec.) | Treatment[c] No Light (L-) | Light (L+) |
|---|---|---|---|---|---|---|---|---|
| 1 | 0 | 0 | N/a | N/a | N/a | N/a | 4 | N/a |
| 2 | 0 | 150 | 706 | 150 | 60 | 400 | 4 | 4 |
| 3 | 250 | 0 | 706 | 150 | 60 | 400 | 4 | 1 (4) |
| 4 | 250 | 150 | 706 | 150 | 60 | 400 | 4 | 0 |
| 5 | 300 | 0 | 706 | 150 | 60 | 400 | 4 | 1 (3) |
| 6 | 300 | 150 | 706 | 150 | 60 | 400 | 4 | 0 |

[a] 1.5x10$^5$/mL
[b] 664 nm
[c] Qualitative score: 0 = 0 colonies, 1 = 1-5, 2 = 6-100, 3 = 101-300, 4 = 301+, (#) = number of colonies
N/a = not applicable

FIGURE 2

Pyrrolnitrin-MB PDT photodestruction of fungi

| Organism[a] | Pyrrolnitrin (μg/mL) | MB (μg/mL) | Power[b] (mW) | Dose rate (mW/cm$^2$) | Light dose (J/cm$^2$) | L- | L+ |
|---|---|---|---|---|---|---|---|
| *Aspergillus flavus* | 50 | 0 | 0 | 0 | 0 | 2 (26)[c] | N/a[d] |
| | 100 | 0 | 0 | 0 | 0 | 1 (1) | N/a |
| | 50 | 100 | 161 | 127 | 20 | 4 | 2 (26) |
| | 100 | 200 | 706 | 558 | 42 | 2 | 1 (1) |
| | 100 | 250 | 706 | 558 | 42 | 2 (6) | 0 |
| *Candida albicans* | 10 | 0 | 0 | 0 | 0 | 3 | N/a |
| | 50 | 0 | 0 | 0 | 0 | 1 (3) | N/a |
| | 15 | 100 | 161 | 127 | 20 | 4 | 2 (10) |
| | 50 | 100 | 161 | 127 | 20 | 4 | 0 |

[a] 1.5x10$^5$/mL
[b] Laser light wave length = 664 nm
[c] Qualitative score: 0 = 0 colonies, 1 = 1-5, 2 = 6-100, 3 = 101-300, 4 = 301+, (#): number of colonies
[d] N/a = not applicable

FIGURE 3

APPARATUS AND METHOD OF PHOTODYNAMIC ERADICATION OF ORGANISMS UTILIZING PYRROLNITRIN

RELATED APPLICATION

This application hereby incorporates by reference and, under 35 U.S.C. §119, claims the benefit of priority of U.S. Provisional Patent Application No. 60/263,125 filed Jan. 19, 2001.

FIELD OF THE INVENTION

The invention relates to a photodynamic therapy (PDT) or process, and more particularly to a photodynamic therapy or process utilizing a photosensitive material and pyrrolnitrin for in vitro and in vivo cellular and acellular organism eradication. The invention also relates to photodynamic eradication of bacteria, fungal, and viral wound infections and sterilization of tissue using a photosensitive material, such as methylene blue, methylene green, or toluidene blue, pyrrolnitrin, and a surfactant material, such as polymyxin B, SDS, cetrimide, or benzalkonium chloride. Additionally, the invention relates to photodynamic eradication of cancer cells, such as present within a tumor, by PDT in conjunction with a photosensitive material and pyrrolnitrin. The present invention advantageously uses light energy in combination with a photosensitive material, pyrrolnitrin, and a surfactant material to treat both in vitro and in vivo pathogens, including cancer cells and microbiological pathogens. The invention also relates to the eradication or destruction of biofilms via a photodynamic mechanism. The invention also relates to an apparatus and method of use for eradication of biofilms on a diverse range of medical products, such as intravascular catheters, endotracheal tubes, and implants. The invention further relates to an apparatus and method of use for eradication of cellular and acellular organisms within an air filtration or air decontamination device for eliminating or reducing harmful biological elements such as viruses, bacteria, and fungus. The invention further relates to the eradication of spores in both in vivo and in vitro applications.

BACKGROUND OF THE INVENTION

Abnormal cells and acellular organisms are known to selectively absorb certain dyes (photosensitive materials) delivered to a treatment site to a more pronounced extent than surrounding tissue. Once presensitized, abnormal cells or acellular organisms can be destroyed by irradiation with light of an appropriate wavelength corresponding to an absorbing wavelength of the photosensitive material, with minimal damage to surrounding normal tissue. This procedure, which is known as photodynamic therapy (PDT), has been clinically used to treat metastatic breast cancer, bladder cancer, head and neck cancers, esophageal cancer, lung cancer, and other types of malignant tumors, actinic keritosis, and macular degeneration.

PDT is generally used to treat hyperproliferating tissues, i.e. cancer, etc, by first administering a photosensitizer to the patient by a suitable route such as by intravenous [IV], intramuscular [IM], intraperitoneal [IP] injection, or oral administration, and then waiting for a predetermined period of time known to be sufficient to effect the preferential uptake and retention of the photosensitizer in the target tissue relative to the concentration of the photosensitizer in normal (non-hyperproliferating) tissues. By permitting time to elapse after systemic administration of the drug, the photosensitizer is generally localized in a variety of tissue/cell types as well as locations within the target tissue. The time for photosensitizer build-up in a target tissue varies but is in the range of 2–24 h. The resulting therapeutic response therefore generally involves a variety of cytological effects.

Photodynamic therapy (PDT) is a treatment that is based upon the differential uptake by cancerous cells of photosensitizing agents, followed by irradiation of the cells to cause a photochemical reaction that is believed to generate chemically disruptive species, such as singlet oxygen. These disruptive species in turn injure the cells through reaction with cell parts, such as cellular and nuclear membranes. Photodynamic therapy has been used successfully for treating several types of cancer cells.

Pyrrolnitrin is a known antibiotic which is particularly effective against fungal pathogens. Pyrrolnitrin is known as 3-Chloro-4-(3-chloro-2-nitrophenyl) pyrrole. Pyrrolnitrin is an antifungal antibiotic isolated from Pseudomonas pyrrocinia. Pyrrolnitrin may be biosynthesized from tryptophan. Proprietary preparations of pyrrolnitrin include MIEUTRIN and MICUTRIN. Another pyrrolnitrin containing compound is provided by Fujisawa Pharmaceutical Co., Ltd. Osaka, Japan.

Pyrrolnitrin is a phenylpyrrole derivative with strong antibiotic activity that has been shown to inhibit a broad range of fungi. Pyrrolnitrin was originally isolated from *Pseudomonas pyrrocinia,* but has since been isolated from Myxococcus species, Burkholdaria species, and several other Pseudomonas species such as Ps fluorescens. The compound has been reported to inhibit fungal respiratory electron transport and uncouple oxidative phosphorylation. It has also been proposed that pyrrolnitrin causes generalized lipoprotein membrane damage.

Air filtration devices and systems are known. Certain air filtration systems provide for eradication of biological pathogens using electromagnetic radiation. However, known electromagnetic radiation pathogen destruction techniques have significant limitations. For example, UV and microwave destruction approaches may only reduce the bacteria count, and not eradicate the pathogens altogether. Furthermore, bacteria may become resistant to UV eradication over relatively short periods of time. Microwave destruction is through generation of severe heat, i.e., 100 C. This modality would not be applicable as a portable biological weapon countermeasure. In comparison, photodynamic therapy antibacterial effects have demonstrated complete destruction and sterilization of highly concentrated bacterial species in vitro and therefore would appear to be superior to the above methods.

Many hospitalized patients, particularly patients in an Intensive Care Unit ("ICU"), must be fitted with endotracheal tubes to facilitate their respiration. An endotracheal tube is an elongate, semi-rigid lumen which is inserted into a patient's nose or throat and projects down into airflow communication with the patient's respiratory system. As such, the patient either directly, or with the aid of a respiratory unit, is able to breathe more effectively through the endotracheal tube. Endotracheal tubes may remain in place within a patient for an extended period of time, e.g. up to a 14 day period. Biofilm contamination of endotracheal tubes within intubated patients may lead to an increased rate of infection, particularly pneumonia. An effective apparatus and method of use for eradication of biofilm organism on endotracheal tubes of intubated patients is desired.

Occurrences of catheter related bloodstream infection (CRBSI) have increased in part as a result of the wide use of invasive medical devices, including intravascular catheters. CRBSI is one of the most common types of nosocomial bloodstream infection, a finding that has been attributed to the wide use of intravascular catheters in hospitalized patients. Recent interventions to control CRBSI include anticoagulant/antimicrobial lock, use of ionic silver at the insertion site, employment of an aseptic hub model, and antimicrobial impregnation of catheters.

Several factors pertaining to the pathogenesis of CRBSI have been identified. The skin and hub are the most common sources of colonization of percutaneous vascular catheters. For short-term, non-nontunneled, noncuffed catheters, the organisms migrate from the skin insertion site along the intercutaneous segment, eventually reaching the intravascular segment of the tip. For long-term catheters, the hub is a major source of colonization of the catheter lumen, which ultimately leads to bloodstream infections through luminal colonization of the intravascular segment.

The catheter surface is another factor relating to the pathogenesis of CRBSI. Organisms that adhere to the catheter surface maintain themselves by producing an "extracellular slime," a substance rich in exopolysaccharides, often referred to as fibrous glycocalyx or microbial biofilm. Microorganisms bind to the surface of host proteins, such as fibrin and fibronectin, to produce biofilm. As described in more detail herein, the organisms embed themselves in the biofilm layer, often becoming more resistant to antimicrobial activity. The use of lumen flush solutions including a combination of antimicrobial agents as well as anti-coagulants is a known process. Another strategy has been to impregnate the surfaces of catheters with antimicrobial agents in order to prevent colonization and the formation of biofilm. An improved approach for prevention of intravascular catheter-related infections is desired.

A considerable amount of attention and study has been directed toward preventing colonization of bacterial and fingal organisms on the surfaces of orthopedic implants by the use of antimicrobial agents, such as antibiotics, bound to the surface of such devices. The objective of such attempts has been to produce a sufficient bacteriostatic or bactericidal action to prevent colonization. Various methods have previously been employed to coat the surfaces of medical devices with an antibiotic.

U.S. Pat. No. 4,442,133, invented by Greco et al., discloses a method to coat the surface of medical devices with antibiotics involving first coating the selected surfaces with benzalkonium chloride followed by ionic bonding of the antibiotic composition. Applicant incorporates by reference herein the teachings of U.S. Pat. No. 4,442,133.

U.S. Pat. No. 4,879,135, invented by Greco et al., discloses surface modification of surgical implants by binding of drugs which, after implantation, are slowly released. More particularly, the invention relates to improved surgical implants having sustained, localized delivery of pharmacological agents such as extended antibiotic activity or reduced thrombogenicity, and methods for producing same. The surface modification of surgical implants by the adhesion thereto of pharmacological agents for the purpose of minimizing infection and prosthesis rejection is well-known and has generated broad interest for some time. Applicant incorporates by reference herein the teachings of U.S. Pat. No. 4,879,135.

Many different approaches have been taken including those disclosed in U.S. Pat. Nos. 4,563,485; 4,581,028; 5,707,366; and 4,612,337, each being incorporated by reference herein.

A biofilm is an accumulation of microorganisms including bacteria, flingi and viruses that are embedded in a polysaccharide matrix and adhere to solid biologic and non-biologic surfaces. Biofilms are medically important as they may account for a majority of microbial infections in the body. Biofilms account for many of the infections of the oral cavity, middle ear, indwelling catheters and tracheal and ventilator tubing. The National Institutes of Health estimates that the formation of biofilms on heart valves, hip and other prostheses, catheters, intrauterine devices, airway and water lines and contact lenses has become a $20 billion dollar health problem in the United States. A treatment apparatus and protocol for the reduction and/or eradication of biofilms is another aspect of the present invention.

Biofilms are remarkably resistant to treatment with conventional topical and intravenous antimicrobial agents. The Center for Biofilm Engineering at Montana State University has reported that biofilms may require 100 to 1,000 times the standard concentration of an antibiotic to control a biofilm infection. This is thought to be due to the antibiotic's inability to penetrate the polysaccharide coating of the biofilm. Even more concerning is that biofilms increase the opportunity for gene transfer due to the commingling of microorganisms. Such gene transfer may convert a previous avirulent commensal organism into a highly virulent and possibly antibiotic resistant organism.

Bacteria embedded within biofilms are also resistant to both immunological and non-specific defense mechanisms of the body. Bacterial contact with a solid surface triggers the expression of a panel of bacterial enzymes that cause the formation of polysaccharides that promote colonization and protection of the bacteria. The polysaccharide structure of biofilms is such that immune responses may be directed only at those antigens found on the outer surface of the biofilm and antibodies and other serum or salivary proteins often fail to penetrate into the biofilm. Also, phagocytes may be effectively prevented from engulfing a bacterium growing within a complex polysaccharide matrix attached to a solid surface.

Nosocomial pneumonia is the most prevalent infection in patients who are mechanically ventilated. It is the leading contributor to mortality in patients, accounting for 50% of deaths in patients with hospital acquired infections. The endotracheal tubes (ET) and tracheostomy tubes have long been recognized as a risk factor for nosocomial pneumonia since they bypass host defenses allowing bacteria direct access to the lungs. These tubes are commonly made of polyvinyl chloride, a surface on which local bacteria colonize rapidly to form an adhesive polysaccharide glycocalyx layer. This glycocalyx layer protects bacterial colonies from both natural and pharmacologic antibacterial agents, in effect increasing the virulence of the bacterial species in the intubated host. This phenomenon of biofilm formation has been demonstrated to occur on ET tubes and subsequent dislodgement of biofilm protected bacteria in the lungs by a suction catheter is considered to be a significant factor in the pathogenesis of nosocomial pneumonia. Indeed, in a study of biofilm formation in endotracheal tubes, microbial biofilm was identified by surface electron microscopy in 29 of 30 endotracheal tubes examined. Interestingly, there was no biofilm formation on the outer surface of the ET tube. Biofilm formed exclusively on the luminal surface of all tubes regardless of whether the patients had received broad spectrum antibiotics and was most prevalent around the side hole of the tip region. ET tubes obtained within 24 hours of placement showed large areas of surface activity with adherent bacteria in a diffuse pattern indicating initial colonization of the ET tube. The surface of tubes in place for longer periods had a profuse microbial biofilm. In some instances a large mass of matrix enclosed bacterial cells appeared to project from the confluent accretion on the luminal surface of the ET tube in such a manner that it could be dislodged readily and aspirated into the lower respiratory tract. Pseudomonas species, Staphylococcus aureus, and enteric aerobic bacteria including E. coli, were the most frequently isolated pathogens in the ET tubes in patients that did not receive broad spectrum antibiotics. These also are the pathogenic bacteria most commonly found in nosocomial pneumonia. In patients that received broad spectrum antibiotics yeast species and Streptococcus species were more common. Evaluations have been made into the relationship of biofilm formation in endotracheal tubes and distant colonization of the pulmonary tree. These evaluations have demonstrated that bacteria from the endotracheal tube biofilm were capable of being cultured from the moisture exchanger and the ventilator tubing up to 45 cm from the tip of the endotracheal tube. Furthermore they demonstrated that contamination of the tracheal tube biofilm with a patient's own gastrointestinal flora provides a mechanism for initial and repeated lung colonization and secondary pneumonia. These life threatening pulmonary infections are perpetuated by microbiological seeding from the tracheostomy and endotracheal tube biofilms and become difficult to treat due to the propensity of the biofilm microorganisms to develop antibiotic resistance. Biofilm contamination of endotracheal tubes within intubated patients may lead to infections or other complications as a result of biofilm organisms.

Catheters used for abdominal cavity tubing drainage bags and various connectors are also common sources of infection. In particular, a high percentage of patients who require long-term urinary catheters develop chronic urinary tract infections. Such patients are at risk of developing bacteremia or chronic pyelonephritis, condition of high morbidity and mortality. Many different medical articles may lead to infection when in contact with a body tissue or fluid. Exemplary of such articles are vascular access (arterial and venous) catheters, introducers, vascular grafts, urinary catheters and associated articles, such as drainage bags and connectors, and abdominal cavity drainage tubing, bags and connectors. A novel apparatus and method of infection prevention for such medical articles is particularly desired.

SUMMARY OF THE INVENTION

The present invention is directed to a photodynamic therapy utilizing a pyrrolnitrin. In particular, a photodynamic therapy of the present invention is particularly adapted for treatment of fungi, bacteria, cancer cells, and other cellular and acellular organisms. One particular fungi group particularly responsive to photodynamic therapy according to the present invention is the Aspergillus group. Yet another fungi responsive to this PDT is *Candida albicans*. In one embodiment of the present invention, an air filtration device is utilized to eradicate airborne pathogens.

The present invention also provides a method of photoeradication of cells and acellular organisms, such as during an in vitro or in vivo disinfection or sterilization procedure, or for cancer cell or acellular organism eradication. In one embodiment, the method utilizes a combination of a photosensitive material, pyrrolnitrin, and a chemical agent, such as a surfactant material, in a solution. The invention additionally provides a method of dispensing a combined solution at or near a cell site and subsequently irradiating the cell site with light at a wavelength absorbed by the photosensitive material. The invention also relates to an apparatus or kit assembly including a photosensitive material, pyrrolnitrin, and/or a surfactant, such as cetrimide, SDS, ARGUARD, or benzalkonium chloride. Yet another aspect of the present invention is the eradication or destruction of biofilms via a photodynamic mechanism.

The invention also relates to a use of a photosensitizing material, such as methylene blue, methylene green, or toluidene blue, in combination with pyrrolnitrin, and a surfactant compound, such as polymyxin B, SDS, ARGUARD, cetrimide or benzalkonium chloride, in a PDT treatment protocol against bacterial, fungal, acellular organism infections, and/or for cancer cell photoeradication. A treatment device is configured to deliver light energy to the area of infection or cancer cell activity at wavelengths ranging from about 450 nm to about 850 nm; provide a dosage rate ranging from about 0 to about 150 mw/cm$^2$; and provide a light dose ranging from 0 to about 300 J/cm$^2$.

The use of a photosensitive material, such as methylene blue, methylene green, or toluidene blue, combined with pyrrolnitrin, and optionally combined with a surfactant material, such as SDS, polymyxin B, cetrimide or benzalkonium chloride, in a photodynamic therapy advantageously acts as a broad spectrum antimicrobial, i.e., antibacterial, antiviral, sporicidal, and/or antifungal agent. PDT utilizing the photosensitizer/pyrrolnitrin/surfactant combination may occur, for example, before a surgical operation. The present invention advantageously results in the destruction of gram positive and gram negative bacteria, fungi, viruses, and spores. Importantly, the present invention acts to destroy antibiotic resistant bacteria and fungi as it utilizes a different destruction mechanism than antibiotics.

The invention also relates to a method of treating an infection including identifying an in vitro or in vivo area of infection; applying or dispensing a concentration including a photosensitive material, such as methylene blue, methylene green, or toluidene blue, pyrrolnitrin, and optionally a surfactant, such as polymyxin B, SDS, cetrimide or benzalkonium chloride, to the area of infection; and exposing the area of infection with a light having a light wavelength, light dosage and a light dosage rate. For toluidene blue, the light wavelength may range from about 560 nm to about 680 nm. For methylene blue, the wavelength may range from about 600 nm to about 670 nm. For methylene green, the wavelength may range from about 600 nm to about 670 nm. The light dosage may range from about 10 J/cm$^2$ to about 60 J/cm$^2$. The light dosage rate may range from about 50 mw/cm$^2$ to about 150 mw/cm$^2$. The concentration for methylene blue, methylene green, and toluidene blue may range from about 10 µg/ml to about 500 µg/ml. Pyrrolnitrin may be provided in a solution having a concentration range from about 25 µg/ml to about 1 g/ml or 0.001% to 5.00%. A more preferred range of pyrrolnitrin is from about 25 µg/ml to 150 µg/ml. For other photosensitive materials, the preferred wavelength or range may be known or available. The area of infection may include gram positive and gram negative bacteria, fungus, spores, or viruses including, but not limited to, at least one of Staphylococcus sp., Aspergillus, *Candida albicans*, *Escherichia coli*, Enterococcus sp., Streptococcus sp., Klebsiella, Serratia, *Pseudomonus aeruginosa, Hemophilus influenzae,* Clostridia sp., Herpes strains, or human immunodeficiency virus (HIV).

The invention also relates to a treatment kit having a solution including at least a combination of a photosensitizing material, such as methylene blue, methylene green, or toluidene blue, and pyrrolnitrin. In addition, the solution may contain a surfactant material, such as polymyxin B, SDS, cetrimide, or benzalkonium chloride. Pyrrolnitrin may be provided in a solution having a concentration range from about 25 µg/ml to about 1 g/ml or 0.001% to 5.00%. A more preferred range of pyrrolnitrin is from about 25 µg/ml to 150 µg/ml. For polymyxin B, the concentration ranges may be from about 3 µg/ml to about 500 µg/ml. For SDS and cetrimide, the concentration range may be from 0.005% to 1%. For benzalkonium chloride, the concentration ranges may be from 0.001% to 1%. A particular concentration range of interest for benzalkonium chloride is from 0.005% to 0.5%. A laser light emitting treatment device may be utilized to effect the photodynamic process, including but not limited to a light source which emits at wavelengths ranging from about 450 nm to about 850 nm; providing a dosage rate ranging from about 10 mw/cm$^2$ to about 150 mw/cm$^2$; and providing a light dose ranging from 5 J/cm$^2$ to about 300 J/cm$^2$. Alternative light sources would also be practicable as appreciated by one skilled in the relevant arts, including but not limited to non-coherent light sources, such as flash bulbs and high intensity lamps.

The invention also relates to a method of treating an infection, an in vitro or in vivo sterilization procedure, or photoeradication of cancer cells, including the steps of providing one or more cells; providing a concentration of combined photosensitive material, pyrrolnitrin, and/or surfactant on or near the one or more cells; and applying a light having a wavelength ranging from about 450 nm to about 850 nm; a dosage rate ranging from about 0 to about 150 mw/cm$^2$; and a light dose ranging from 0 to about 300 J/cm$^2$ to the one or more cells wherein the combination of light and photosensitive material is adapted to cause photodestruction of the one or more cells. The one or more cells may be an infection caused by or associated with a bacteria, virus, or fungus. Alternatively, the one or more cells may be cancer cells. Virus infected cells may also be treated in accordance with the present invention. In such instance, a virus within the cell may be specifically eradicated without destruction of the host cell. Obligate intracellular bacterial agents, such as Chlamydia, Rickettsia, and Ehrlichia, may be treated in accordance with the present invention. Other bacteria may also be treated in accordance with the present invention. The one or more cells may be gram positive or gram negative bacteria. The photosensitive material may be methylene blue, methylene green, toluidene blue, or a combination thereof. The photosensitive material may be monomeric, dimeric, or polymeric.

Another aspect of the present invention is a photodynamic method of biofilm reduction and/or eradication on medical devices. A wide variety of medical devices may be utilized to practice aspects of the present invention. Such devices may include implants (temporary or permanent), endotracheal tubes, catheters (venous and arterial), grafts, shunts, heart valves, orthopedic prostheses, intraocular prostheses, profusion pumps, sutures, and associated articles, such as connectors and tubing. A particular aspect of the present invention is to provide an effective apparatus and method of use for eradication of biofilm organism on endotracheal tubes within intubated patients. Alternative medical devices may be processed by teachings of the present invention to photodynamically eradicate organisms upon the devices.

Methylene blue (MB) based photodynamic therapy has been demonstrated in vitro and in vivo to be effective in the photoeradication of some antibiotic resistant gram positive and gram negative bacteria. In general, methylene blue based photodynamic therapy has limited applicability toward destruction of gram negative bacteria and fungi, such as Aspergillus. Methylene blue has a very low tissue toxicity and can be administered to humans orally and intravenously in high doses without any toxic effects. Because of the known low toxicity and its present use and acceptance in medical practice as well as its high photoactive potential this photosensitive material is ideal use in accordance with the present invention for evaluation of its effect on the destruction of bacteria, viruses and fungi. The photoactive dye methylene blue belongs to the phenothiazine class. Its bactericidal effect is related to its photodynamic properties. This dye is a single pure compound and has a strong absorption at wavelengths longer than 610 nm, where light penetration into tissue is optimal. The absorbance peaks of MB are at 611 nm and 664 nm, its optical extinction coefficient is 81600 M$^{-1}$ cm$^{-1}$. MB has a high quantum yield of the triplet state formation (~T=0.52–0.58) and a high yield of the singlet oxygen generation (0.2 at pH 5 and 0.94 at pH 9).

The photoactivity of MB results in two types of photooxidations: (i) direct reaction between the photoexcited dye and substrate by hydrogen abstraction or electron transfer creating different active radical products; and (ii) direct reaction between the photoexcited dye in triplet state and molecular oxygen producing singlet oxygen. Both kinds of active generated products are strong oxidizers and they cause cellular damage, membrane lysis, protein inactivation and/or DNA modification.

Biofilms are resistant to topical, oral and intravenous antibiotic administration due to the polysaccharide glycocalyx formation that surrounds the bacteria. The polysaccharide coating prevents the antibiotic from penetrating into the biofilms and destroying the bacteria. Methylene blue has the potential ability to destroy biofilms as it selectively binds and penetrates polysaccharides thereby exposing the bacteria in the biofilm to the photodestructive effects of methylene blue. For this reason, methylene blue may be an ideal photosensitizer that may provide a means for the broad spectrum photoeradication of biofilms. The use of a surfactant, such as SDS or benzalkonium chloride, can act to both emulsify the biofilm and increase a membrane permeability of an acellular or cellular organism within the biofihn. The combination of a surfactant with a photosensitive material permits the photosensitive material to pass through the biofilm and acellular or cellular organism membrane, and accumulate within the acellular or cellular organism.

Another aspect of the present invention is the provision of an apparatus for eradicating airborne pathogens. A filtration device may be utilized to capture airborne biological organisms. As described herein, the filtration device may include a variety of different structures, including a small portable device to be worn by a user, to a large building air filtration device within a HVAC system. In one embodiment, photodynamic eradication of captured organisms is performed within the filtration device for eradicating the pathogen. The pathogens may include a variety of cellular and acellular organisms, including but not limited to bacteria, viruses, and fungi. Biological agents of significant concern include anthrax, tularemia, plague, Aspergillus fungi, and small pox. These biological agents should be susceptible to eradication by photodynamic therapy treatment.

Another aspect of the present invention concerns an air purification system utilizing photodynamic therapy (PDT) broad spectrum destruction of microbiological organisms. One significant application of the technology would be as a defense system against a biological weapons attack, as the broad spectrum destruction of bacteria, fungi, and viruses would offer an increased level of protection. Additional suitable applications include: temporary building environments, vehicular applications, and portable mask form.

A photodynamic air filtration device utilizing aspects of the present invention may associate pathogens with a photosensitive material and pyrrolnitrin and subsequently illuminate the pathogen/photosensitizer/pyrrolnitrin combination to achieve photodynamic eradication. In one example, a rotating filter may be used to capture pathogens for transfer into a photosensitizer/pyrrolnitrin solution. The photosensitizer solution may be selected from among a group of photosensitive materials. The pathogens and photosensitizer/pyrrolnitrin solution are subsequently illuminated by a light source, such as a VCSEL array, LED's, a laser diode array or an incandescent bulb, to achieve the desired organism eradication. The device could be battery powered to provide field operability.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawings and description are to be regarded as illustrative in nature, and not as restrictive.

BRIEF DESCRIPTION OF THE FIGURES

FIG. 2 is a table of results of photodynamic eradication of *Aspergillus flavus* on a filter material using a combined solution of methylene blue and pyrrolnitrin.

FIG. 3 is a table of results of photodynamic eradication of *Aspergillus flavus* and *Candida albicans* using a combined solution with methylene blue and pyrrolnitrin.

DESCRIPTION OF THE PRESENT INVENTION

In accordance with the invention, a photodynamic therapy utilizes a photosensitive material, such as methylene blue, methylene green, or toluidene blue, in combination with pyrrolnitrin, and a light emitting device, such as a light wand, light patch, light pad or shaped light-emitting or light-communicating article. As described in more detail herein, the photodynamic therapy may be achieved at a variety of cells sites, including but not limited to tissue fields and air filtration devices.

The photodynamic therapy according to the present invention may be utilized in the eradication of cellular organisms, such as tumor cells, cancer cells, virus-infected cells, bacteria, etc. The photodynamic therapy according to the present invention may also be utilized in the eradication of acellular organisms, defined broadly to include organisms not composed of cells, e.g., bodies of protoplasm made discrete by an enveloping membrane (also referred to a capsule, envelope, or capsid). Examples of acellular organisms include, but are not limited to, viruses, spores, fungi, and other virus-like agents such as viroids, plasmids, prions, and virinos, and other infectious particles.

Figure 1:
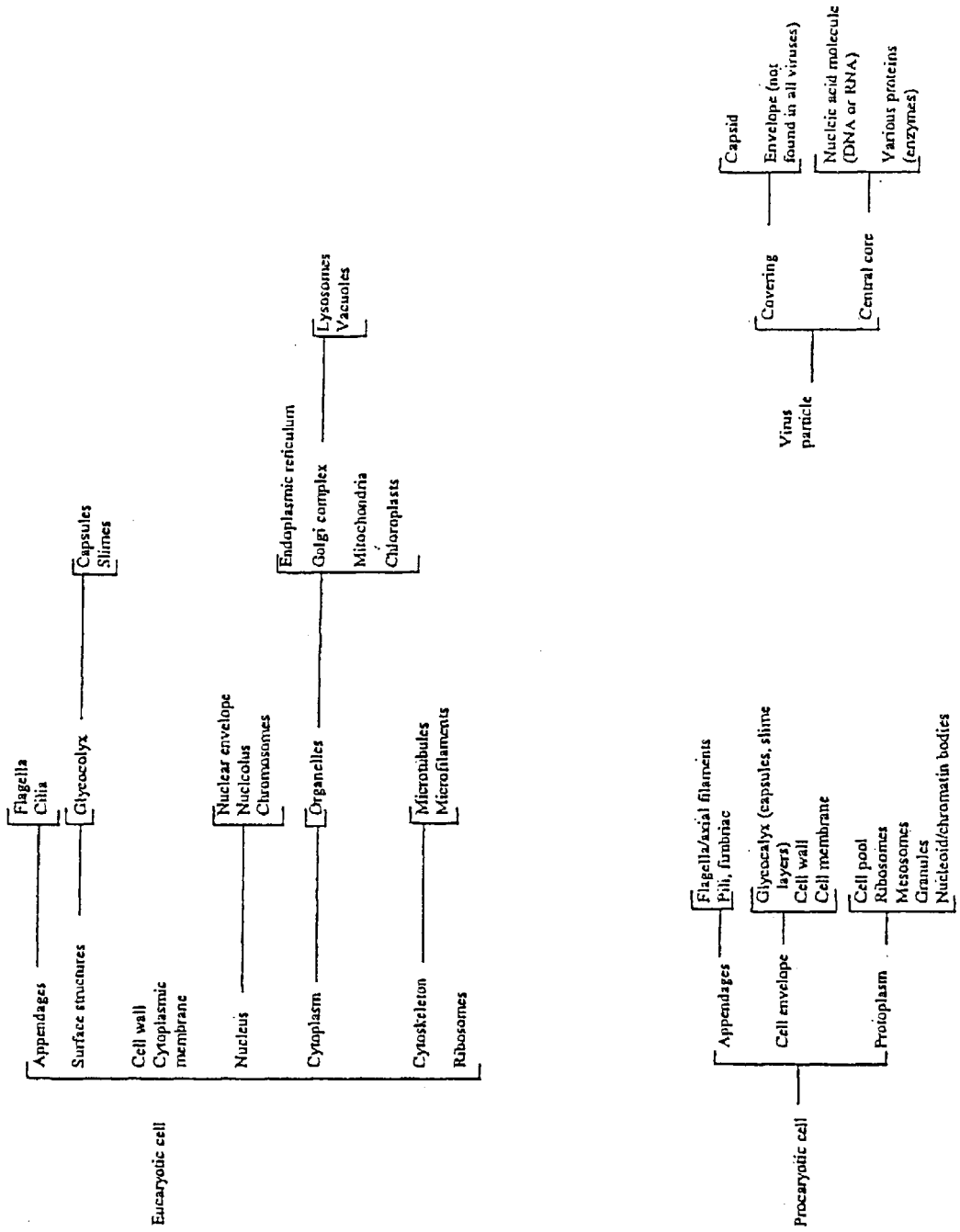
FIG. 1 is a tree structure of organisms.

Reference may be made to FIG. 1, wherein component structures of acellular and cellular organisms are presented. Procaryotic cells are cellular organisms, including bacteria. The component structures of procaryotic cells include appendages, cell envelope, and protoplasm. The cell envelope further includes the glycocalyx (capsules, slime layers), cell wall, and cell membrane. All bacteria cells invariably have a cell envelope, glycocalyx, cell membrane, cell pool, ribosomes, and a nucleoid; the majority have a cell wall. Although they are common to many species, flagella, pili, fimbriae, capsules, slime layers, and granules are not universal components of all bacteria. Organisms of the genera Chlamydia, Rickettsia, and Ehrlichea, referred to as obligate intracellular bacteria, are prokaryotes that differ from most other bacteria with respect to their very small size and obligate intracellular parasitism.

Eucaryotic cells are typical of certain microbial groups (fungi, algae, protozoans, and helminth worms) as well as all animal and plant cells. Eucaryotic cells have component structures including appendages, surface structures, cell wall, cytoplasmic membrane, nucleus, cytoplasm, cytoskeleton, and ribosomes. The surface structures may include glycocalyx, capsules, and slimes. Virus particles are not cells and they neither possess procaryotic nor eucaryotic structural qualities. Instead, they are large, complex macromolecules, with parts made up of repeating molecular subunits. Virus particles include component structures of a covering and a central core. The covering includes a capsid and in some viruses, an envelope. All viruses have a protein capsid or shell that surrounds the nucleic acid strand. Members of 12 of the 17 families of animal viruses possess an additional covering external to the capsid called an envelope, which is actually a modified piece of the host's cell membrane. Viruses that lack this envelope are considered naked nucleocapsids. Special virus-like infectious agents include the prion (proteinacious infectious particles) and viroids.

A photosensitive material is defined herein as a material, element, chemical, solution, compound, matter, or substance which is sensitive, reactive, receptive, or responsive to light energy. Photosensitive materials may be provided in a liquid, gaseous, or solid form, including but not limited to liquids, solutions, topical ointments, or powders. Photosensitive materials for use in accordance with the present invention are generally non-toxic to the target cellular or acellular organisms and surrounding tissues at concentrations envisaged. However, there is no particular requirement that the photosensitive material should be non-toxic to the microbes. Particular photosensitive materials which may be used in accordance with the invention include methylene blue, methylene green, and toluidene blue. Additional photosensitive materials are also identified herein.

Pyrrolnitrin is a known antibiotic which is particularly effective against fungal pathogens. Pyrrolnitrin is known as 3-Chloro-4-(3-chloro-2-nitrophenyl) pyrrole. Pyrrolnitrin is an antifungal antibiotic isolated from Pseudomonas pyrrocinia. Pyrrolnitrin may be biosynthesized from tryptophan. Proprietary preparations of pyrrolnitrin include MIEUTRIN and MICUTRIN. Another pyrrolnitrin containing compound is provided by Fujisawa Pharmaceutical Co., Ltd. Osaka, Japan.

Pyrrolnitrin is a phenylpyrrole derivative with strong antibiotic activity that has been shown to inhibit a broad range of fungi. Pyrrolnitrin was originally isolated from Pseudomonas pyrrocinia, but has since been isolated from Myxococcus species, Burkholdaria species, and several other Pseudomonas species such as Ps fluorescens.

The terms "chemical agent" and "surface acting agents" and "surfactants" as used herein are broadly defined to include materials, compounds, agents, chemicals, solutions, or substances which alter the energy relationships at molecular interfaces. Among the manifestations of these altered energy relationships is the lowering of surface or interfacial tensions. Chemical agents or compounds displaying surface activity are characterized by an appropriate structural balance between one or more water-attracting groups and one or more water-repellent groups. Surfactants are characterized by having two different moieties, one polar and the other nonpolar. The polar moeity is referred to as hydrophilic or lipophobic, and the nonpolar as hydrophobic or lipophilic. The electrical charge on the hydrophilic portion of a surface acting agent may serve as a convenient basis of classification of these compounds. Surface active agents have been classified as: Anionic, Cationic, Non-Ionic, and Amphoteric. Other classes of surfactants are also known or may be developed or defined in the future. Chemical agents, such as surfactants, are known to affect the permeability of cell membranes, and membrane-like structures of acellular organisms, such capsids and envelopes. The ability of these chemical agents or surfactants to become oriented between lipid and protein films is thought to produce a disorientation of the membrane of microorganisms, so that it no longer functions as an effective osmotic barrier. The term 'membrane' as used herein is meant to broadly include cellular or acellular organism structures, such as cell walls, cytoplasmic membranes, cell envelopes, coverings, capsids, envelopes, or other types of boundary-defining terms of cellular or acellular organisms. It is believed that a photosensitive material may diffuse through the membrane of a microorganism having a surfactant-compromised membrane. A photosensitive material concentration within the membrane and the organism increases over time via osmotic diffusion of the photosensitive material across the surfactant-compromised membrane.

The polymyxins, colisimethate, and the polyene antifingal agents nystatin and amphotericin are surfactants, as is sodium dodecyl sulfate (SDS). Cetrimide is also a known surfactant. Benzalkonium chloride, having synonyms of n-alkyl dimethyl benzyl ammonium chloride solution, parasterol, alkyl dimethyl benzylammonium chloride, and zephiran chloride, is also a known surfactant. Benzalkonium chloride is a cationic surfactant, having a known use as a medical disinfectant.

A light source is utilized to practice embodiments of the present invention. The light source may be laser light source, a high intensity flash lamp, light emitting diode (LED) or other illumination sources as appreciated by those skilled in the relevant arts. A broad spectrum light source may be utilized, however a narrow spectrum light source is one preferred light source. The light source may be selected with reference to the specific photosensitive material, as photosensitive materials may have an associated range of photoactivation. A laser light source may be used to practice the present invention. A variety of laser light sources are currently available, and the selection of a particular laser light source for implementing the PDT would readily be appreciated by those skilled in the relevant arts. A laser source may be selected with regard to the choice of wavelength, beam diameter, exposure time and sensitivity of the cellular and/or acellular organisms. In preferred embodiments, the light source is utilized for a period of time necessary to affect a photodynamic response. The period of time for photodynamic activation of the photosensitive material is preferably between 5 seconds and 1 hour. Yet more preferably, the period of time for light illumination is between 2 and 20 minutes.

A variety of light delivery devices may be utilized to practice the present invention. A hand manipulable light wand or fiber optic device may be used to illuminate tissue within a living body. Such fiber optic devices may include a disposable fiber optic guide provided in kit form with a solution containing a photosensitive material and a surfactant. Other potential light devices for use in accordance with the present invention include the devices disclosed in applicant's U.S. Pat. No. 6,159,236, entitled Expandable treatment device for photodynamic therapy and method of using same, and U.S. Pat. No. 6,048,359, entitled Spatial orientation and light sources and method of using same for medical diagnosis and photodynamic therapy, both incorporated in their entireties by reference herein. Yet another light delivery scheme is envisioned, wherein a medical device or prosthesis is utilized to communicate light from an external light source to a cell site within a patient, particularly a biofilm cell site on a surface of the prosthesis. A translucent or transparent prosthesis body may be provided to receive light at a first location and communicate light to interior surfaces which support a biofilm. A variety of light communication schemes utilizing at least a portion of the prosthesis body have been envisioned.

Repeat administrations of a treatment protocol may also be necessary or desired, including repeat administrations of pyrrolnitrin and/or photosensitive materials and light activation. The repeat administrations may include different photosensitive materials and/or different pyrrolnitrin-containing compounds than earlier administered. Repeat administrations of the treatment protocol may continue for a period of time.

Additional aspects of the present invention include different administration or delivery approaches of the photosensitive material and the pyrrolnitrin. In one exarnple, the photosensitive material and pyrrolnitrin are provided in a combined solution and topically applied to the cell site. In alternative embodiments, the photosensitive material may be applied or delivered or dispensed to a tissue or cell site before, during, or after the application or delivery of pyrrolnitrin through known delivery/administration approaches.

Additional aspects of the present invention further include combinations of different photosensitive materials, pyrrolnitrin, and surfactants during a treatment protocol. In one preferred embodiment, a particular combination of a photosensitizer, pyrrolnitrin, and a surfactant would be applied to the cell site in association with a photodynamic illumination of the tissue site. Yet other aspects of the invention include combining a plurality of different surfactants with a given photosensitive material and/or pyrrolnitrin.

The present invention is directed to a photodynamic eradication of fungi, bacteria, cancer cells, and acellular organisms, utilizing a combination of a photosensitive material and pyrrolnitrin. Another aspect of the present invention is a combination of a photosensitive material, pyrrolnitrin and a surfactant. The disclosure of Applicant's copending patent applications, U.S. Ser. Nos. 09/514,070 and 09/792,578 relating to photosensitive materials and surfactants, are incorporated by reference herein. Additionally, the disclosure of Applicant's copending patent application U.S. Ser. No. 10/026,198, relating to photosensitive materials and benzalkonium chloride, is also incorporated by reference herein.

Pyrrolnitrin may be provided as a singular agent, or as a component of a compound. Pyrrolnitrin may be provided in a solution having a concentration range from about 25 $\mu$g/ml to about 1 g/ml or 0.001% to 5.00%. One particularly effective photosensitizing agent for use in combination with pyrrolnitrin is methylene blue. One particular surfactant is SDS.

A treatment kit may include a solution of at least a combination of a photosensitizing material, such as methylene blue, methylene green, or toluidene blue, and pyrrolnitrin. In addition, the solution may contain a surfactant material, such as polymyxin B, SDS, ARGUARD, cetrimide, or benzalkonium chloride. Pyrrolnitrin may be provided in a solution having a concentration range from about 25 µg/ml to about 1 g/ml or 0.001% to 5.00%. For polymyxin B, the concentration ranges may be from about 3 µg/ml to about 500 µg/ml. For SDS and cetrimide, the concentration range may be from 0.005% to 1%. For benzalkonium chloride, the concentration ranges may be from 0.001% to 1%. A particular concentration range of interest for benzalkonium chloride is from 0.005% to 0.5%. A laser light emitting treatment device may be utilized to effect the photodynamic process, including but not limited to a light source which emits at wavelengths ranging from about 450 nm to about 850 nm; providing a dosage rate ranging from about 10 mw/cm$^2$ to about 150 mw/cm$^2$; and providing a light dose ranging from 5 J/cm$^2$ to about 300 J/cm$^2$. Alternative light sources would also be practicable as appreciated by one skilled in the relevant arts, including but not limited to non-coherent light sources, such as LED's, flash bulbs and high intensity lamps.

PDT eradication of pathogenic bacteria, fungi and viruses has been demonstrated in vitro and in vivo using a short term exposure to an appropriate photosensitizer and pyrrolnitrin and laser light. Due to the affinity of the photosensitizer to the cell membrane as well as cell DNA, the activation of the photosensitizer by the red light results in the irreversible damage of the pathogenic microorganism's cell wall and membrane as well as DNA disruption resulting in cell death with the inability of the organisms to develop resistance. Pyrrolnitrin may be an effective potentiating agent for photodynamic air filtration via cell eradication.

Methylene blue may be used as a photosensitive material. Methylene blue has a high photoactive potential and has an absorbance peak at 665±7 nm.

Known photosensitive materials which may find applicability in practicing the present invention include, but are not limited to, the following:

| PHOTOSENSITIVE MATERIAL | WAVELENGTH |
| --- | --- |
| Hypiricin | 550–660 nm |
| Aluminum phthalocyanine | 670–675 nm |
| Merocyanine | 500–560 nm |
| Psoralen | 320–400 nm |
| Rose Bengal | 548 nm |
| Acridine orange | 489 nm |
| Indocyanine green | 660 nm |
| Nile blue | 628 nm |
| Nile red | 553 nm |
| Toluidene | 560–660 nm |
| Methylene green | 600–670 nm |
| Lutetium Texaphyrin | 732 nm |
| Benzporphyrin derivative | 690 nm |
| Foscan (mTHPC) | 652 nm |
| Tin ethyl etiopurpurin | 664 nm |
| Photofrin (porfimer solution) | 630 nm |
| Aminolevulinic Acid | 630 nm |

Eradication of *Aspergillus flavus* on a filter material using methylene blue and pyrrolnitrin mediated photodynamic therapy: (FIG. 2)

Materials and Methods:

Prior to experiments, fresh *Aspergillus flavus* was grown on Sabouraud Dextrose Agar (Remel, Inc., Lenexa, Kans.). Methylene blue (87%, Sigma-Aldrich, St. Louis, Mo.) was dissolved into 0.45% respiratory saline for final concentrations of 250 or 300 μg/mL and pyrrolnitrin was dissolved into ethanol (final conc. 20% ethanol) for a final concentration of 150 μg/mL. *Aspergillus flavus* was the added at a concentration of $1.5\times10^8$/mL in 0.45% saline to each test tube. The stock solution of *Aspergillus flavus* was cultured onto Sab-Dex agar (Remel, Inc., Lenexa, Kans.) using a Calgiswab type 4 for qualitative growth assessment and comparison with photodynamic therapy treated filters. An amount of 0.2 mL of the experimental solutions were pipetted onto standard filter paper and underwent light activation using 664 nm diode laser light (DD2 and DD4 models, Miravant, Inc., Santa Barbara, Cailf.) using a microlens and a spot size of 3 cm at a power of 706 mW, a dose rate of 150 $mW/cm^2$, and a light dose of 60 $J/cm^2$ for 400 seconds. Upon completion of light activation the filter paper was cultured for qualitative growth onto Sab-Dex agar. Plates were sealed using shrink seal bands (Remel, Inc., Lenexa, Kans.) and grown aerobically at 37° C. for 48 hours. Results were visually scored using the following qualitative scoring system: 0=no colonies, 1=1–5 colonies, 2 =6–100 colonies, 3=101–300 colonies, 4=301+colonies, ( )=number of colonies.

The results of this investigation, particularly tests (4) and (6), demonstrate that the combined solution including pyrrolnitrin and methylene blue effectively sensitized *Aspergillus flavus* and its spores to killing by laser irradiation. As a result, an efficacious treatment for eradicating such fungi and spores would include the steps of disposing a solution containing methylene blue and pyrrolnitrin at a cell site and illuminating the site with a light source effective to initiate a photodynamic response.

Photoeradication of *Aspergillus flavus* and *Candida albicans* using methylene blue and pyrrolnitrin: (FIG. 3)

Materials and Methods:

Aspergillus experiment

Prior to experiments, fresh *Aspergillus flavus* was grown on Sabouraud Dextrose Agar (Remel, Inc., Lenexa, Kans.). Methylene blue (87%, Sigma-Aldrich, St. Louis, Mo.) was dissolved into 0.45% respiratory saline and pyrrolnitrin was dissolved into ethanol (final conc. 20% ethanol). Total volumes of either 0.5 or 1 mL were used for all experiments. One experiment evaluated the efficacy of pyrrolnitrin alone at 25, 50, 100, 150, 200 μg/mL. In addition, 20% ethanol without pyrrolnitrin or methylene blue was tested. In PDT experiments, methylene blue was added to each test tube for final concentrations of 100, 200, 250, 300 μg/mL. Pyrrolnitrin was added at one of the following concentrations to each test tube: 15, 20, 30, 40, 50, 100, 150 μg/mL. An amount of 0.25 mL of *A. flavus* at a concentration of $1.5\times10^8$/mL in 0.45% saline was added to each test tube. In experiments involving SDS (Sigma-Aldrich, St. Louis, Mo.), 0.1 mL of SDS was added for a final concentration of 0.01%. In experiments involving cetrimide (Sigma-Aldrich, St. Louis, Mo.), cetrimide was added at various volumes for final concentrations of 0.03, 0.2, 0.3, 0.5%. 0.05 or 0.035 mL of the experimental solutions in glass test tubes underwent light activation using 664 nm diode laser light (DD2 and DD4 models, Miravant, Inc., Santa Barbara, Calif.) using a microlens and a spot size of 1.27 cm at a power of 161 mW, a dose rate of 127 $mW/cm^2$, and a light dose of 20 $J/cm^2$ for 157 seconds or a power of 190 mW, a dose rate of 150 $mW/cm^2$, and a light dose of 60 J/m² for 400 seconds or a power of 706 mW, a dose rate 558 mW/cm², and light dose of either 20 or 42 J/cm² for either 37.5 or 75 seconds. Test tubes were irradiated from the bottom at a 4 cm distance from the microlens fiber. Upon completion of light activation test tubes were cultured for qualitative growth onto Sab-Dex (Remel, Inc., Lenexa, Kans.), the plates were sealed using shrink seal bands (Remel, Inc., Lenexa, Kans.), and grown aerobically at 37° C. for 48 hours. Results were visually scored using the following qualitative scoring system: 0=no colonies, 1=1–5 colonies, 2=6–100 colonies, 3=101–300 colonies, 4=301+colonies.

Candida experiment

Prior to experiments, fresh *Candida albicans* was grown on Sabouraud Dextrose Agar (Remel, Inc., Lenexa, Kans.). Methylene blue (87%, Sigma-Aldrich, St. Louis, Mo.) was dissolved into 0.45% respiratory saline and pyrrolnitrin was dissolved into ethanol (final conc. 20% ethanol). A total volume of 0.5 mL was used for all experiments. Two experiments evaluated the efficacy of pyrrolnitrin alone at 5, 10, 15, 20, 25, 50, 100, 150, 200 µg/mL. In addition, 2.5% and 20% ethanol without pyrrolnitrin or methylene blue were tested. In PDT experiments, methylene blue was added at a volume of 0.125 mL to each test tube for a final concentration of 100 µg/mL. Pyrrolnitrin was added at one of the following concentrations to each test tube: 0, 15, 25, and 50, µg/mL. 0.25 mL *C. albicans* at a concentration of $1.5 \times 10^8$/mL in 0.45% saline was added to each test tube. An amount of 0.05 mL of the experimental solutions in glass test tubes underwent light activation using 664 nm diode laser light (DD2 and DD4 models, Miravant, Inc., Santa Barbara, Calif.) using a microlens and a spot size of 1.27 cm at a power of 161 mW, a dose rate of 127 mW/cm², and a light dose of 20 J/cm² for 157 seconds. Test tubes were irradiated from the bottom at a 4 cm distance from the microlens fiber. Upon completion of light activation test tubes were cultured for qualitative growth onto Sab-Dex (Remel, Inc., Lenexa, Kans.) and grown aerobically at 37° C. for 24 hours. Results were visually scored using the following qualitative scoring system: 0=no colonies, 1=1–5 colonies, 2=6–100 colonies, 3=101–300 colonies, 4=301+colonies.

The results of these investigations demonstrated that the solution including pyrrolnitrin and methylene blue sensitized *Aspergillus flavus* and *Candida Albicans* to killing by laser irradiation. As a result, an efficacious treatment for eradicating such fungi would include the steps of disposing a solution containing methylene blue and pyrrolnitrin at a cell site and illuminating the site with a light source effective to initiate a photodynamic response.

Photoeradication of Cells within an Air Filtration Device using methylene blue and pyrrolnitrin: (FIG. 4)

The reduction or elimination of airborne contaminants is desirable, if not essential, in some environments. The increasing threat of the use of biological weapons requires systems for the rapid and complete broad spectrum eradication of pathogens. Although many different gram positive and gram negative bacteria, fungal, or viral pathogens may be employed as biological weapons, the present threats include anthrax, tularemia, plague, Aspergillus, and small pox. The reduction of airborne pathogens in commercial HVAC systems similarly requires rapid and complete broad spectrum eradication of these pathogens.

One embodiment of the present invention is directed to an apparatus for eradicating airborne biological pathogens using a photosensitizer and pyrrolnitrin solution, a light source, a method for commingling the pathogens with the photosensitizer/pyrrolnitrin solution, and subsequent light exposure of the pathogen/photosensitizer/pyrrolnitrin mixture at sufficient energy levels at a predetermined wavelength. The photosensitizer may be selected from among a group of photosensitive materials. The light source may be an array of vertical cavity surface-emitting lasers (VCSELs), LEDs, laser diodes, or one or more incandescent bulb(s).

Figure 4:
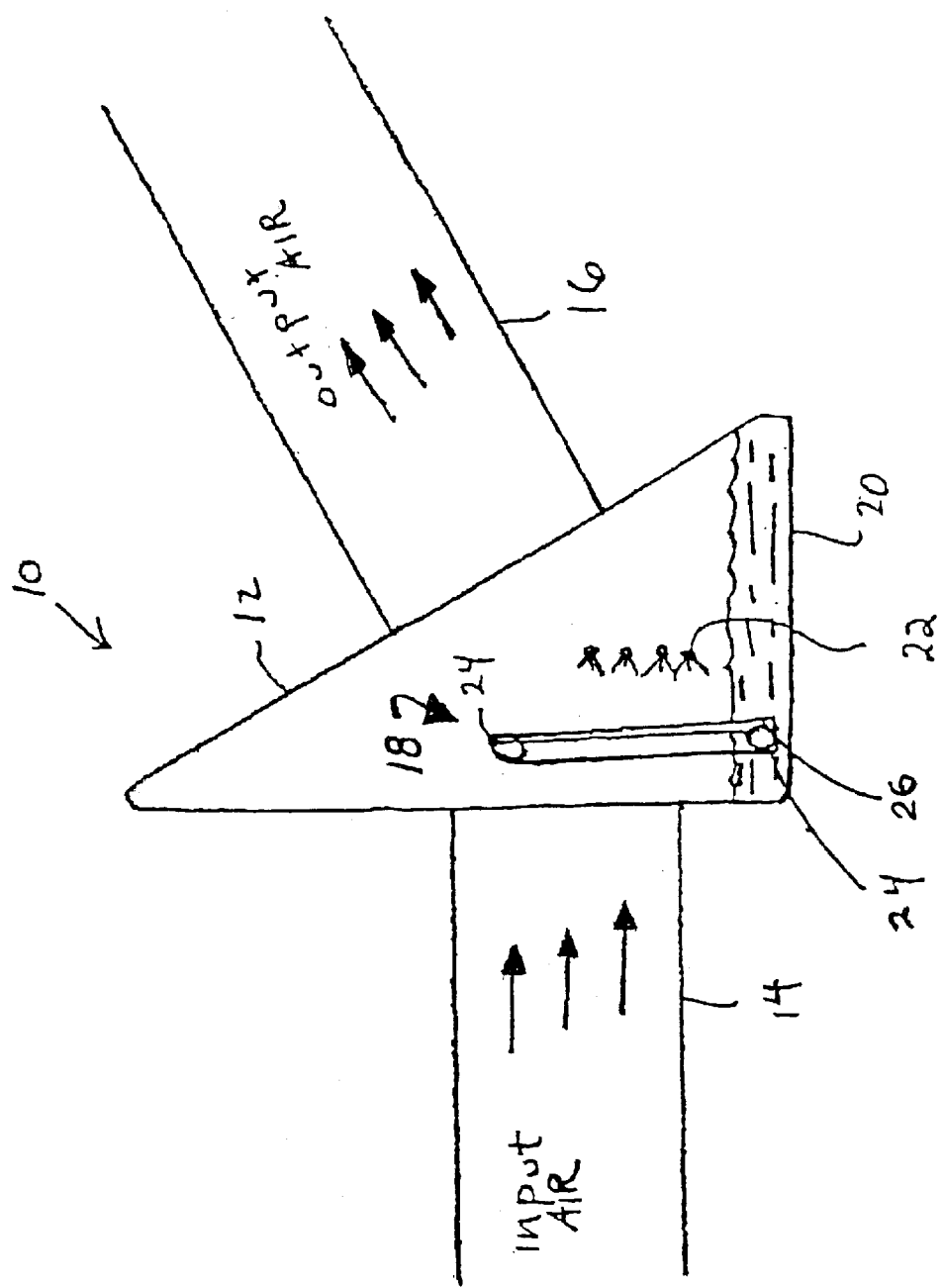
FIG. 4 is a depiction of an air filtration/decontamination device utilizing a photodynamic reaction for organism eradication, using a photosensitive material and pyrrolnitrin.

Referring to FIG. 4, an air filtration device 10 according to the present invention is illustrated. The device 10 includes an enclosure structure 12 for housing the internal components of the filter 10 and for facilitating transportability of the device 10. The enclosure 12 illustrated may be sized for a building structure and may be placed in-line within the heating—air conditioning—ventilation (HVAC) system of the structure. Airflow through the enclosure 12 enters through an air intake 14 and exits through an air outlet 16. A driven fan or other air motive means (not shown) may be placed in any suitable location within the HVAC system.

Within the enclosure 12 of the device 10 is a filter structure 18, a bath solution 20 including a photosensitive material, pyrrolnitrin, an optionally a surfactant such as SDS, cetrimide, or benzalkonium chloride, and a light source 22 such as a VCSEL array. The filter structure 18 may be a flexible roll structure and may be maintained between rotating rollers 24 which impart a rotating motion to the roll 18. The lower end 26 of the roll structure 18 may be received into the bath solution 20 which bathes that portion of the filter structure 18. The filter 18 is positioned to entrap incoming bacteria, fungi, or virus elements within its structure. The entrapped elements are then passed through the bath solution 20 as the filter 18 rotates about the rollers 24. The entrapped elements, then partially or completely enveloped with the bath solution 20 are subjected to illumination from the light source 22 to neutralize the elements.

Filter structures other than the flexible roll structure 18 may be used. For example, a generally flat disc-like filter may be rotated about its axis in a bath solution 20 or even a stationary filter (with photosensitizer being applied upon) may be practicable. The bath solution 20 may be sprayed or otherwise applied to the surface of the filter structure 18 in a variety of known manners which are readily appreciated by those skilled in the art. The filter structure 18 may be replaceable or may be sealed within a disposable enclosure. Sizing of the entire filter 10 can result in the application of the filter technology in a variety of environments, such as building structures, vehicle environments, portable structures, or even in human mask form.

Figure 5:
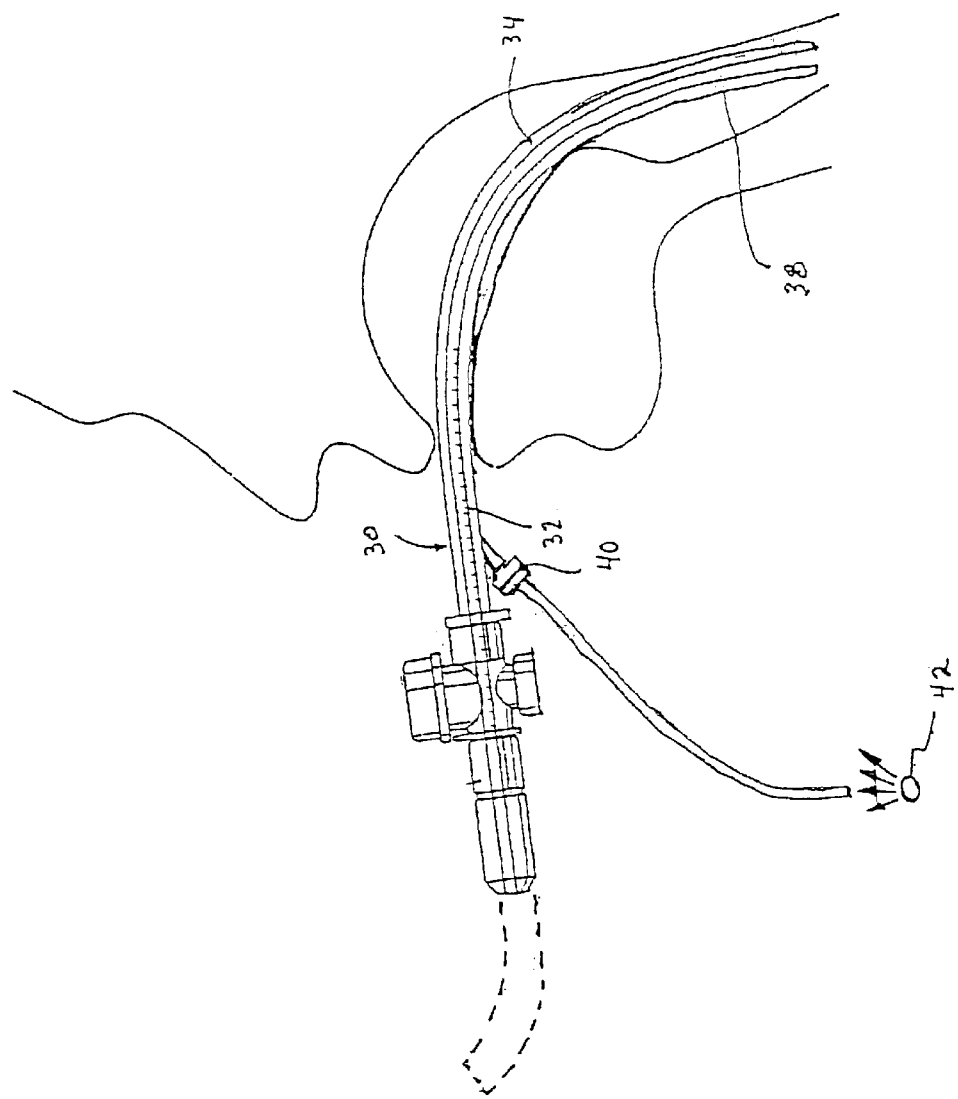
FIG. 5 is a depiction of an endotracheal tube within an intubated patient illustrated biofilm eradication aspects of the present invention.

Photoeradication of Cells upon a Medical Device using methylene blue and pyrrolnitrin: (FIG. 5)

Additional aspects of the present invention further include a prosthesis or other medical device, wherein the medical has a solution or compound including one or all of a photosensitive material, pyrrolnitrin, and optionally a surfactant, such as benzalkonium chloride, provided at or near a surface of the prosthesis, particularly at a surface capable of supporting a biofilm. The solution or compound may be provided at or near the surface of the prosthesis via known bonding or impregnation techniques, or may be provided during other manufacturing steps of the product. The term "medical device" employed herein and throughout the specification and claims is intended to broadly include, though not be limited to, devices used to replace or assist a body part or bodily function, including:

Intravenous, peritoneal dialysis, parenteral and urological catheters;

Endotracheal tubes or respiration related devices;

Vascular grafts;
Ventricular and peritonovenous shunts;
Heart valves;
Orthopedic prostheses;
Intraocular prostheses;
Profusion pumps;
Sutures;
Prostheses used in reconstructive plastic surgery; and
Implantable devices.

A photodynamic eradication of organisms upon a medical device surface may be achieved by light illumination via a light source such as a laser, LED light, VCSEL device, flash bulbs, lamps, etc. Photodynamic eradication of organisms upon a medical device surface may be via internal illumination of the prosthesis using an remote light source. In envisioned embodiments, the prosthesis may be a transparent or translucent material for internally communicating light to a chemically-treated (photosensitive material and surfactant) surface of the prosthesis.

In another preferred embodiment, a photosensitive material such as methylene blue, methylene green, or toluidene blue may be used in combination with pyrrolnitrin, and surfactants, such as SDS, polymyxin B, ARGUARD, cetrimide, or benzalkonium chloride, and activated by light energy to provide broad spectrum antibiotic activity for destroying both gram positive and gram-negative bacteria, funguses, viruses, spores, and/or cancer cells. The photosensitive material, pyrrolnitrin, and surfactant may be combined in solution and administered to a site to be treated. Solution administration may include topical application, inhalation, and/or intravenous, subcutaneous, intratumoral, or peritumoral injection. The photosensitive material, pyrrolnitrin, and surfactant may also be provided via a chemical release from an impregnated surface of a medical article. Other surface binding approaches may be appreciated for associating the photosensitive material, pyrrolnitrin, and the surfactant at a surface of the medical article. Additional administration approaches may also be practicable. An intratumoral injection of the solution may be advantageous for photoeradication of tumor cells.

Another aspect of the present invention is the provision of biofilm reduction and/or eradication. A biofilm is an accumulation of microorganisms including bacteria, fungi and viruses that are embedded in a polysaccharide matrix and adhere to solid biologic and non-biologic surfaces. Biofilms are medically important as they may account for a majority of microbial infections in the body. Biofilms account for many of the infections of the oral cavity, middle ear, indwelling catheters and tracheal and ventilator tubing.

The use of a surfactant, such as SDS or benzalkonium chloride, in combination with pyrrolnitrin and a photosensitive material, such as methylene blue or methylene green, may be useful in treating biofilms. One treatment for eradicating a microorganism of a biofilm according to the present invention may include the steps of disposing a solution containing a methylene blue, pyrrolnitrin, and benzalkonium chloride at a cell site and illuminating the cell site with a light source effective to initiate a photodynamic therapy. Other photosensitive materials and surfactants may also find applicability to such a treatment.

Yet another aspect of the present invention is the use of a photosensitive material, pyrrolnitrin, and optionally a surfactant, together used in a photodynamic process as a broad spectrum cellular and acellular organism agent for sterilizing medical equipment and devices, such as intravascular catheters, endotracheal tubes, catheters, and endoscopes, from viruses, bacteria, fungi, and spores. A particular application of a sterilization process may include the steps of: (i) providing or disposing a photosensitive material, pyrrolnitrin, and benzalkonium chloride on or upon a tangible apparatus; and (ii) illuminating the apparatus with light at an appropriate wavelength and light dosage to effect a photodynamic reaction for eradicating the cellular and acellular organisms. Pyrrolnitrin may be provided in a solution having a concentration range from about 25 $\mu$g/ml to about 1 g/ml or 0.001% to 5.00%. A more preferred range of pyrrolnitrin is from about 25 $\mu$g/ml to 150 $\mu$g/ml. Benzalkonium chloride concentrations may range from 0.001% to 1%. A more preferred range of benzalkonium chloride concentration would be between 0.005% to 0.05%.

One method of practicing the invention may include sterilization of medical equipment, such as an endotracheal tube, intravascular catheters, via biofilm eradication including the steps of: (i) providing a photosensitive material, such as methylene blue, methylene green, toluidene blue, etc., pyrrolnitrin, and optionally a surfactant, such as SDS, cetrimide, ARGUARD, or benzalkonium chloride, on surfaces of the endotracheal tube having biofilm contamination; and (ii) illuminating the endotracheal tube with light at an appropriate wavelength and light dosage to effect a photodynamic eradication of cellular and/or acellular organisms in the biofilm. It is envisioned that additional combinations of photosensitive material, pyrrolnitrin, and surfactant may be utilized to practice this application of biofilm/surface organism eradication.

Another aspect of the present invention is directed toward an endotracheal tube disinfection apparatus and method of use. Endotracheal tubes are well known to those skilled in the relevant arts. In particular, an endotracheal tube 30 utilized to enable a patient to breathe is generally inserted down the throat of a patient as illustrated in FIG. 5. Such an endotracheal tube 30 is preferably of the type including an air flow passage 32 having an interior wall surface 34 that defines its interior diameter. In one embodiment of the present invention, the endotracheal tube 30 is formed from a translucent or transparent material capable of communicating light from a light source to a cell site 38. Surfaces of the endotracheal tube may have a photosensitive material, pyrrolnitrin, and/or a surfactant, such as benzalkonium chloride, impregnated thereupon or bonded thereto. Those skilled in the relevant arts would appreciate the known surface impregnation or bonding techniques toward such end.

The cell site 38 may be a biofilm layer disposed on surfaces of the endotracheal tube 30, such as the tube lumen. A surface-released photosensitive material, pyrrolnitrin, and surfactant may be utilized to achieve a photodynamic reaction at the cell site 38. In this regard, the photosensitive material, pyrrolnitrin, and surfactant are released from the surfaces of the endotracheal tube and associate with organisms of the biofilm. A photodynamic eradication of organisms within the biofilm matrix may then be achieved by illuminating the biofilm organisms with appropriate light. In one embodiment as illustrated in FIG. 5, the endotracheal tube 30 may includes a light port 40 for coupling a light source 42 to the tube 30 wherein the tube body is capable of communicating light from the source 42 to the cell site 38. In an alternative embodiment, the endotracheal tube 30 may include a port (not shown) for receiving a fiber optic line having a light emitting end, wherein the fiber optic line is passed within the interior lumen of the tube to position the light emitting end at a location proximate the biofilm cell site.

In alternative embodiments, the combination of a photosensitive material, pyrrolnitrin, and optionally a surfactant may be provided in solution and disposed at the cell site 38 in a variety of manners, such as via a fluid line 46 or other fluid structure communicating the solution from a source 48 to a surface of the endotracheal tube (See, FIG. 5). Alternatively, a solution containing a photosensitive material, pyrrolnitrin, and optionally selected surfactant may be communicated within an interior structure of the endotracheal tube 30 and be transferred to the biofilm matrix of the cell site 38 via one or more apertures (not shown) in the tube 30 wall.

A method of photodynamic eradication of biofilm organisms on a medical device may include the steps of:

providing a medical device having light communicative properties within the patient, wherein one or more surfaces of the medical device have an associated photosensitive material and pyrrolnitrin, and without or without (optionally) a surfactant;

allowing the photosensitive material, pyrrolnitrin, and optional surfactant to be released from a medical device surface and react with the biofilm organisms;

providing a source of light illumination having predetermined light characteristics; and illuminating the biofilm layer with the light source to achieve a photodynamic reaction resulting in the eradication of organisms within the biofilm layer.

The process as described above may be periodically repeated to photodynamically eradicate organisms upon the medical device. The illumination may be with a light source providing a specific light wavelength, light dosage and a light dosage rate. The light wavelength may range from about 580 nm to about 680 nm. The light dosage may range from about 10 J/cm$^2$ to about 60 J/cm$^2$. The light dosage rate may range from about 50 mw/cm$^2$ to about 150 mw/cm$^2$. A similar process may be utilized for eradicating organisms upon an intravascular catheter or other medical devices or prosthesis.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A method of photoeradication of cells comprising the steps of:
    identifying an area of cell activity;
    providing pyrrolnitrin and a photosensitive material to the area of cell activity; and
    exposing the area of cell activity to a light having a light wavelength, light dosage and a light dosage rate to cause disruption of the cells.

2. The method of photoeradication of cells of claim 1 wherein the light wavelength ranges from about 400 nm to about 800 nm, the light dosage ranges from about 10 J/cm$^2$ to about 100 J/cm$^2$ and the light dosage rate ranges from about 50 mw/cm$^2$ to about 200 mw/cm$^2$.

3. The method of photoeradication of cells of claim 1 wherein the wavelength ranges from about 300 nm to about 700 nm.

4. The method of photoeradication of cells of claim 1 wherein the photosensitive material is methylene blue.

5. The method of photoeradication of cells of claim 4 wherein a concentration range of the methylene blue is from about 5 μg/ml to about 500 μg/ml.

6. The method of photoeradication of cells of claim 1 wherein a concentration range of the pyrrolnitrin is from about 25 μg/ml to about 1 g/ml.

7. The method of photoeradication of cells of claim 6 wherein a concentration range of the pyrrolnitrin is from about 25 μg/ml to about 150 μg/ml.

8. The method of photoeradication of cells of claim of claim 1 wherein the pyrrolnitrin is disposed in a combination of different pyrrolnitrin-containing compounds.

9. The method of photoeradication of cells of claim 1 wherein the step of providing pyrrolnitrin and the photosensitive material is achieved via one or more of the group containing an intravenous injection, an injection proximate the area of cell activity, inhalation administration, a topical administration, a subcutaneous injection, and an injection within the area of cell activity.

10. The method of photoeradication of cells of claim 1 further comprising the step of applying a surfactant to the area of cell activity.

11. The method of claim 10, wherein the surfactant is selected from among a group including: cetrimide, SDS, ARGUARD, polymyxin B, and benzalkonium chloride.

12. The method of claim 1 wherein the area of cell activity is associated with one of the following: a sterilization procedure, a biofilm eradication procedure, an infection treatment procedure, a cancer tissue site, and an air filtration device.

13. A photodynamic therapy treatment kit comprising:
    a volume of a concentration including a combination of pyrrolnitrin and a photosensitive material; and
    a light emitting treatment device configured to emit light.

14. The treatment kit according to claim 13 wherein the concentration includes more than one photosensitive material.

15. The treatment kit of claim 13 wherein the concentration further includes a surfactant.

16. The treatment kit of claim 15 wherein the surfactant is selected from among a group including: cetrimide, SDS, polymyxin B, and benzalkonium chloride.

17. The treatment kit according to claim 13 wherein the light emitting treatment device is configured to emit light at wavelengths ranging from about 450 nm to about 850 nm; and to provide a dosage rate ranging from about 0 to about 150 mw/cm2 and a light dose ranging from 0 to about 300 J/cm2.

18. The treatment kit of claim 13 wherein a concentration range of the pyrrolnitrin is from about 25 μg/ml to about 1 g/ml.

19. A method of treatment comprising:
    providing one or more cells;
    providing a concentration in proximity to the one or more cells, said concentration including a combination of pyrrolnitrin and a photosensitive material; and
    applying a light in proximity to the one or more cells, wherein the combination of the light and the pyrrolnitrin and the photosensitive material causes disruption of the one or more cells.

20. The method of treatment of claim 19 wherein the concentration further includes a surfactant.

21. The method of treatment of claim 19 wherein the step of providing the concentration is achieved via one or more of the group containing: an injection proximate to the one or more cells, an intravenous injection, an inhalation administration, a topical application, an injection into a group of one or more cells, and a subcutaneous injection.

22. The method of treatment of claim 19 wherein the one or more cells include at least one of a microbe, a bacteria, a fungus, or a cancer cell.

23. The method of treatment of claim 19 wherein the photosensitive material is at least one of methylene blue, methylene green, toluidene blue, or combinations thereof, and the light is provided at a wavelength ranging from about 450 nm to about 850 nm; a dosage rate ranging from about 0 to about 150 mw/cm2; and a light dose ranging from 0 to about 300 J/cm2.

24. The method of treatment of claim 19 wherein a concentration range of the pyrrolnitrin is from about 25 μg/ml to about 1 g/ml.

25. The method of treatment of claim 19 wherein the step of providing one or more cells is associated with a sterilization procedure.

26. The method of treatment of claim 19 wherein the step of providing one or more cells is associated with an air filtration device.

27. The method of treatment of claim 19 wherein the step of providing one or more cells is associated with treatment of an infection at a tissue site.

28. The method of treatment of claim 19 wherein the step of providing one or more cells is associated with a biofilm site.

29. The method of treatment according to claim 19 wherein the combination includes more than one pyrrolnitrin-containing compound.

30. The method of treatment according to claim 19 wherein the combination includes more than one photosensitive material.

31. The method of treatment according to claim 19 wherein the combination includes more than one pyrrolnitrin-containing compound and more than one photosensitive material.

32. A method of photodynamic disruption of acellular organisms comprising the steps of:
    identifying an area of acellular organism activity;
    applying a concentration including a combination of pyrrolnitrin and a photosensitive material to the area of acellular organism activity; and
    exposing the area of acellular organism activity to light having a light wavelength, light dosage and a light dosage rate.

33. The method of photodynamic disruption of acellular organisms of claim 32, wherein the step of identifying an area of acellular organism activity includes an examination of a portion of a living body.

34. The method of photodynamic disruption of acellular organisms of claim 32, wherein the light wavelength ranges from about 400 nm to about 800 nm, the light dosage ranges from about 10 J/cm$^2$ to about 300 J/cm$^2$ and the light dosage rate ranges from about 50 mw/cm$^2$ to about 200 mw/cm$^2$.

35. The method of photodynamic disruption of acellular organisms of claim 32 wherein the wavelength ranges from about 300 nm to about 700 nm.

36. The method of photodynamic disruption of acellular organisms of claim 32 wherein the pyrrolnitrin is provided in a solution having a concentration range of between 0.001% to 5.00%.

37. The method of photodynamic disruption of acellular organisms of claim 32 wherein the step of identifying an area of acellular activity includes the step of identifying an area of fungal activity.

38. A treatment protocol for a living body having cancer cells, said protocol comprising the steps of:
    identifying cancer cells within the living body;
    administering pyrrolnitrin to the living body;
    administering a photosensitive material to the living body; and
    applying a light in proximity to the cancer cells, the combination of photosensitive material and light resulting in disruption of the cancer cells.

39. The treatment protocol according to claim 38 wherein the steps of administering pyrrolnitrin and photosensitive material to the body are achieved by providing a solution having the pyrrolnitrin and the photosensitive material and disposing the solution on at least a portion of the body.

40. The treatment protocol of claim 39 wherein the step of disposing the solution on at least a portion of the body includes a solution administration selected from the group consisting of: topical administration, intravenous administration, subcutaneous administration, inhalation administration, administration proximate to the cancer cells, and administration within the cancer cells.

41. The treatment protocol according to claim 38 wherein the step of administering the photosensitive material to the body includes the step of providing a solution having a plurality of different photosensitive materials.

42. A method of cell disruption for use in an air filtration device, said method comprising:
    providing a plurality of cells upon an air filtration substrate;
    disposing a pyrrolnitrin-containing material in proximity to the plurality of cells;
    disposing a photosensitive material in proximity to the plurality of cells; and
    applying a light in proximity to the one or more cells to cause disruption of the plurality of cells.

43. The method of cell disruption of claim 42 wherein the plurality of cells are particular cells from among a group containing a microbe, a bacteria, a fungus, and a cancer cell.

44. The method of cell disruption of claim 42 wherein the photosensitive material is selected with specific reference to the plurality of cells.

45. The method of cell disruption of claim 42 wherein the photosensitive material is methylene blue.

46. The method of cell disruption of claim 42 wherein a concentration range of the pyrrolnitrin is from about 25 µg/ml to about 1 g/ml.

47. The method of cell disruption of claim 42 further comprising the step of disposing a surfactant in proximity to the plurality of cells.

48. The method of cell disruption of claim 42 wherein the air filtration substrate is disposed in a HVAC system of a structure.

49. A method of photodynamic eradication of organisms within a biofilm of a medical device, said method comprising the steps of:
    providing a photosensitive material and pyrrolnitrin to a surface of the medical device supporting a biofilm;
    providing a source of light illumination having predetermined light characteristics; and
    illuminating the biofilm layer with the light source to achieve a photodynamic eradication of organisms within the biofilm layer.

50. The method of claim 49 wherein the step of providing the photosensitive material and pyrrolnitrin is via an impregnation of compounds upon a surface of the medical device.

51. The method of claim 49 wherein the step of illuminating the biofilm layer is achieved by an internal illumination of the medical device.

52. The method of claim 49 wherein the step of illuminating the biofilm layer is achieved by an external light source illuminating the biofilm layer.

53. The method of claim 49 further comprising the step of providing a surfactant to the surface of the medical device.

54. The method of claim 53 wherein the surfactant is selected from among the group including: AGUARD, cetrimide, SDS, polymyxin B, and benzalkonium chloride.

55. The method of claim 49 wherein a concentration range of the pyrrolnitrin is from about 25 µg/ml to about 1 g/ml.

* * * * *